United States Patent [19]

Schetters et al.

[11] Patent Number: 4,876,189
[45] Date of Patent: Oct. 24, 1989

[54] PROCESS FOR THE QUANTIFICATION OF CELL POPULATIONS OR SUBPOPULATIONS AND A REAGENT SUITABLE THEREFOR

[75] Inventors: Hartmut Schetters, Munich; Josef Endl, Gilching; Winfried Albert, Pahl, all of Fed. Rep. of Germany

[73] Assignee: Boehringer Mannheim GmbH, Mannheim, Fed. Rep. of Germany

[21] Appl. No.: 927,803

[22] Filed: Nov. 5, 1986

[30] Foreign Application Priority Data

Nov. 19, 1985 [DE] Fed. Rep. of Germany ....... 3541033

[51] Int. Cl.$^4$ ................ G01N 33/545; G01N 33/547; G01N 33/552; G01N 33/577
[52] U.S. Cl. .......................................... 435/7; 435/18; 435/21; 435/25; 435/28; 435/29; 435/34; 435/810; 436/10; 436/519; 436/523; 436/527; 436/533; 436/534; 436/548
[58] Field of Search ................... 435/7, 18, 21, 25, 28, 435/29, 34, 810; 436/10, 519, 527, 533, 534, 548, 523

[56] References Cited

U.S. PATENT DOCUMENTS

| | | | |
|---|---|---|---|
| 4,381,295 | 4/1983 | Kung et al. | 435/7 |
| 4,415,700 | 11/1983 | Batz et al. | 524/548 |
| 4,418,152 | 11/1983 | Hosaka et al. | 436/533 |
| 4,486,530 | 12/1984 | David et al. | 435/7 |
| 4,714,682 | 12/1987 | Schwartz | 436/19 |

OTHER PUBLICATIONS

Johnson et al., In Weir(ED.), *Handbook of Experimental Immunology*, 3rd Ed., Blackwell Scientific Publications, Oxford, 1978, pp. 15.1–15.17.
Nibbering et al., in Bullock et al., (EDS.), *Techniques in Immunocytochemistry*, vol. 3, Academic Press, London, 1982, pp. 97–113.
Knapp, in Wick et al., (EDS.), *Immunofluorescence Technology*, Elsevier Biomedical Press, Amsterdam, 1982, pp. 12–25.

*Primary Examiner*—Sam Rosen
*Assistant Examiner*—David A. Saunders
*Attorney, Agent, or Firm*—Felfe & Lynch

[57] ABSTRACT

A process for quantification of cell populations or subpopulations, by incubating a sample with labelled antibodies directed against characteristic surface antigens of the cell population to be quantified to form labelled antibody/antigen complexes. Standards with known, differing particle concentration and having comparable sedimentation behavior to the cells to be determined and further, carrying molecules which are directed against the labelled antibody or a part hereof are also incubated with the labelled antibodies. The cells of the sample solution, as well as the particles of the standard solution, are separated off from the excess labelled antibodies and the amount of the labelling is measured not only on the cells but also on the particles. By comparison of the measurement value from the sample with the measurement values from the standard solutions, there is ascertained the number of cells to be determined in the sample. The standard and a reagent kit for carrying out the process are also the subject of this application.

11 Claims, 3 Drawing Sheets

PROCESS FOR THE QUANTIFICATION OF CELL POPULATIONS OR SUBPOPULATIONS AND A REAGENT SUITABLE THEREFOR

The present invention is concerned with a process for the quantification of cell populations or subpopulations, especially blood cells, as well as with a reagent for carrying out the process.

The process according to the present invention is especially suitable for the determination of lymphocytes, in particular T-lymphocytes or their subpopulations, the T-helper and T-suppressor cells.

T-lymphocytes have regulatory functions for the humoral as well as for the cellular immune system. They are classified according to developmental stages and function. In the case of T-cells, various maturation stages, as well as sub-groups, must be differentiated. These can be characterised by surface antigens, which are specific for individual developmental stages and for functional sub-groups. Classifications are possible, on the one hand, according to functional criteria and, on the other hand, by serological discrimination. By means of comparisons of the various antigen compositions, conclusions can be drawn regarding the cell populations and thus regarding the instant immune state of the donor.

The dormant T-cells must first be stimulated by antigen before they can be functionally active. Thus, the T-helper cells stimulate the B-lymphocytes to proliferate, to differentiate and to produce antibodies. From the lymphoid cells series, they also activate the macrophages and the T-suppressor cells which are stimulated to the cytotoxic reaction against cells with specific surface antigens.

In the activated state, T-suppressor lymphocytes bring about the suppression of the antibody production and the reaction of autologous T-cells in the desired lymphocyte culture. The T-suppressor cells also show cytotoxic reaction against the target cells after sensitisation with HLA antigen-carrying cells (HLA=human leukocyte antigen).

The usual concentrations in the blood, as well as the quotient of T-helper and T-suppressor cells, lie in the following ranges:

| T-lymphocytes (total) | 0.5–1.5 | $10^6$ cells/ml. blood |
|---|---|---|
| T-suppressor | 0.15–0.45 | $10^6$ cells/ml. blood |
| T-helper | 0.3–0.9 | $10^6$ cells/ml. blood |
| T-helper/T-suppressor | 1.2–3.9 | |

Various diseases can bring about displacements in the composition of the T-cell subpopulations in which the production of a population is reduced or strengthened. These changes occur very early in the course of the disease. Such diseases include, for example, diseases of the rheumatic complex, autoimmune diseases (e.g. rheumatic arthritis, systemic lupus erythemetosus), infectious diseases (e.g. AIDS and viral and fungal infectious diseases) and malignant T-cell diseases (e.g. leukemias and lymphomas).

The determination of the immune status, i.e. the totality of the T-lymphocytes and the relative proportion of the T-helper and of the T-suppressor cells, thus provides a considerable diagnostic advance.

The previous methods of determination for cell populations and subpopulations consist preponderantly in the coloration of the cells with antibodies of corresponding specificity which are labelled with fluorescent dyestuff and the counting thereof under a fluorescence microscope. It is obvious that this is a very laborious and personnel-intensive method and only permits a subjective assessment.

This principle can be mechanised and objectivated with the help of a "fluorescent activated cell sorter" (FACS). In this way, the mechanical counting can admittedly be omitted. However, the method involves a considerable expense for apparatus and requires highly qualified personnel for the operation.

It is an object of the present invention to provide a simpler method with which not only the total number of the cell population but also of certain subpopulation can be determined.

Thus, according to the present invention, there is provided a process for the quantification of cell populations or subpopulations, wherein a sample with the cell population to be determined is incubated with labelled antibodies which are specifically directed against characteristic surface antigens of the cell population to be quantified, one or more standards with known, differing particle concentration are incubated with the same labelled antibodies in the same way, the standard solution consisting of particles which, in their sedimentation behaviour, are comparable with the cells to be determined and are loaded with molecules which are directed against the labelled antibody or a part thereof, the cells of the sample solution, as well as the particles of the standard solution, are separated off from the excess labelled antibodies, the amounts of the labelling is measured not only on the cells but also on the particles and by comparison of the measurement value from the sample with the measurement values from the standard solutions, there is ascertained the number of cells to be determined in the sample.

The process according to the present invention is generally usable in order to quantify cell populations and subpopulations, the method being especially useful for the quantification of blood cells and particularly of lymphocytes. The process has proved to be especially advantageous for the determination of the total number of the T-cells and of the T-helper and T-suppressor subpopulations. Thus, there can be achieved a dependable and precise statement regarding the instant immune status for the diagnosis and control of the course of the therapy.

As antibodies which are directed against antigens, which are characteristic for the cell population to be determined (cell surface antigens), there can be used not only polyclonal but also monoclonal antibodies. There can be used the complete antibodies or also antibody fragments. The monoclonal antibodies are especially preferred.

For labelling the antibodies used, various known methods are available. There can be used all conventional labelling agents, for example radioisotopes, dyestuffs, fluorescent dyestuffs and enzymes. According to the present invention, labelling with enzyme is especially preferred. As labelling enzymes, there can be employed, for example, peroxidase, alkaline phosphatase, glucose oxidase or especially preferably β-galactosidase.

The test is preferably carried out as an antibody binding test and preferably as a solid phase immunoassay. As solid phase, there are used the cells to be determined or the particles of the standard which possess a size and density or a sedimentation behaviour similar to the cells.

In the development of the test, it was an especial difficulty to find a standard which can imitate the properties of lymphocytes so that lymphocytes can be replaced by these. The standard is to possess the advantages of a natural lymphocyte standard without, however, having its disadvantages: lymphocytes are not available to the needed extent, lymphocytes are non-uniform, which results in a deficient reproducability from batch to batch and lymphocytes are not sufficiently stable, which gives rise to problems with regard to storage stability of a lymphocyte standard.

All these disadvantages could be overcome by a standard with artificial particles.

As such particles are preferred small spheroids which can consist of glass or synthetic resin. Especially advantageous are synthetic resin particles, particularly latex particles, which are built up on the basis of methacrylate. These particles should preferably have a diameter of 1-20 μm. and especially of 7-13 μm.

On to the standard particles are coupled molecules (proteins) which are directed against the labelled antibodies or a part thereof. On the one hand, they can be proteins which possess the same antigenic action as the surface antigens on the cells to be determined. However, the particles can also carry anti-antibodies which are directed against the labelled antibodies and preferably against the $F_c$ part of this antibody. Finally, on the particles there can also be present antibodies which specifically recognise the labelling, for example, in the case of an enzyme labelling, the enzyme.

The present invention also provides a standard for the quantification of cell populations or subpopulations, wherein it contains particles which are similar in their sedimentation behaviour to the cells to be determined and carry molecules which are directed against the labelled antibody or a part hereof.

For the preparation of this standard, the particles are first activated, for example with sodium periodate. Subsequently, a part of the activated particles is coupled with a non-specific antibody, for example sheep IgG, according to known methods. The other part of the activated particles is linked with the molecule directly specifically against the labelled antibody or against a part hereof. By mixing various proportions of these two differently labelled particle types, standard solutions are produced which are constant with regard to their particle number but vary with regard to the bound specific molecules. The exact concentration of specific molecules in a particular standard can be determined by comparison with a known lymphocyte concentration which has been determined by conventional counting out using immune fluorescence or with the help of a cell sorter. The binding ability of the so calibrated particles corresponds to a definite number of the cell population or subpopulation to be determined.

The standard can be present as a solution or as a lyophilisate. Before use, the lyophilisate must be resuspended in an appropriate solvent, for example double distilled water.

The present invention also provides a reagent mixture for carrying out the process according to the present invention, wherein it contains the labelled antibody which is specifically directed against the cell population to be determined, one or more standards, an appropriate detection system for the measurement of the labelling agent, as well as further adjuvants possibly necessary.

The individual components are also preferably present in lyophilised form. Before use, they must be resuspended in an appropriate solvent, for example double distilled water.

Figure 1:
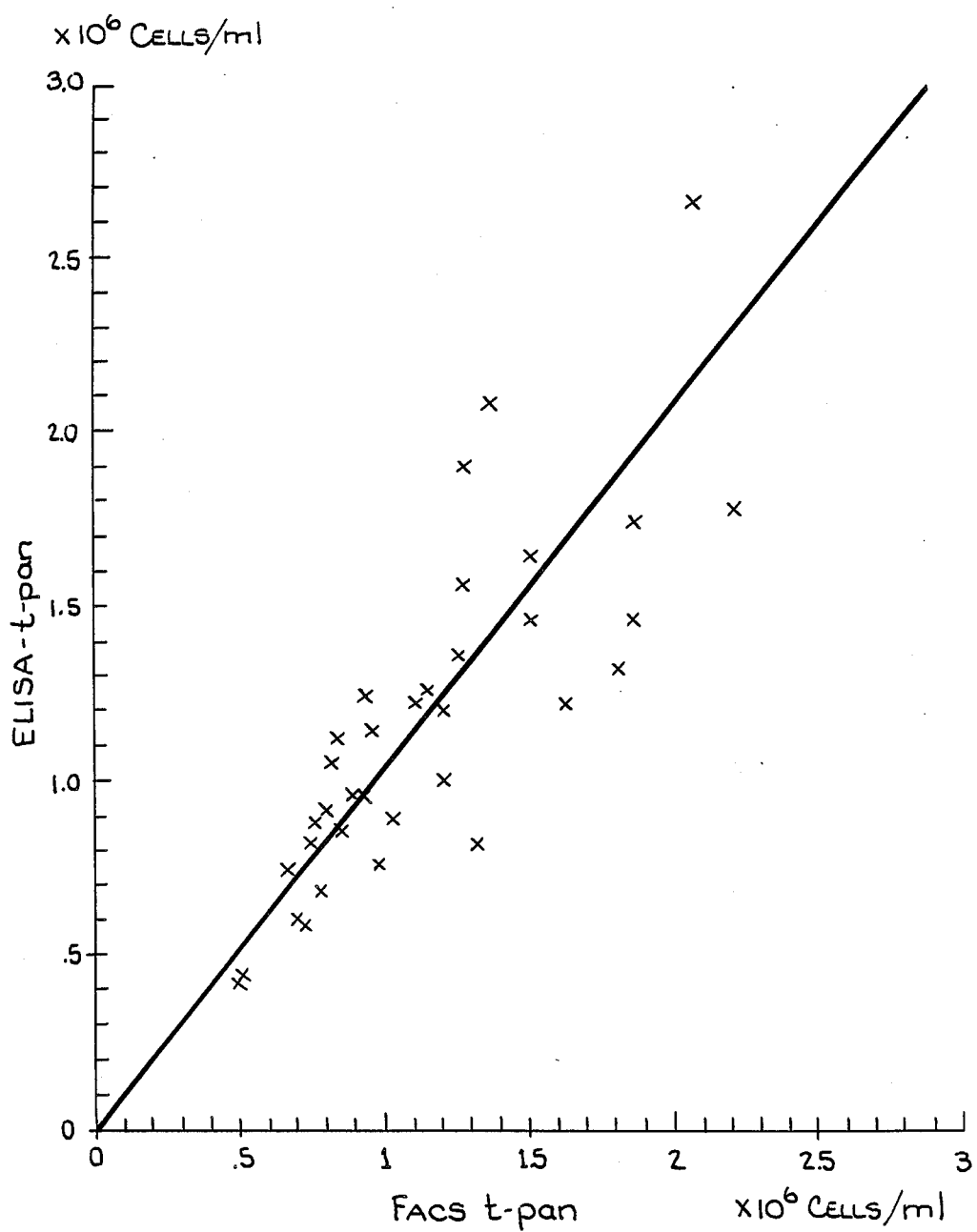
FIG. 1 shows a method comparison FACS/process according to the present invention for total T-lymphocytes (t-pan)

The following Examples are given for the purpose of illustrating the present invention:

EXAMPLE 1

Determination of the total number of T-lymphocytes

1. Preparation of the solutions (a) Standard solutions

Latex particles based on methacrylate (prepared according to Federal Republic of Germany Patent Specification No. 30 48 883 corresponding to U.S. Pat. No. 4,415,700) are activated at pH 5.0 with sodium periodate. The activated latex particles are divided into two halves. One half is coupled with non-specific sheep IgG and the other half with sheep IgG anti-mouse IgG. By mixing these two batches in various defined proportions, three standard solutions are prepared which correspond to a lymphocyte concentration of $0.45 \times 10^6$, $1.56 \times 10^6$ and $3.36 \times 10^6$ cells/ml. The solutions are lyophilised and, in this form, are stable for a comparatively long time. Before use, the standards are resuspended in double distilled water (calibration standard suspensions a, b and c).

(b) Wash buffer 1.47 g. disodium hydrogen phosphate ($Na_2HPO_4.2H_2O$), 0.27 g. sodium dihydrogen phosphate ($NaH_2PO_4.H_2O$) and 8.77 g. sodium chloride are dissolved in double distilled water and made up to 1 liter with water. To this solution are added 0.2% w/v bovine serum albumin and 0.1% w/v sodium azide. For storage, it is lyophilised. Before use, the lyophilisate is resuspended in double distilled water.

(c) Antibody conjugate

Monoclonal antibody CD 6 (M-T411, characterised in detail in: P. Rieber et al., in Leucocyte typing (A. Bernard et al., ed.) 1984, page 303-311, pub. Springer Verlag, Berlin, New York) is coupled with β-D galactosidase and lyophilised. Per determination, there are used 0.025 U, dissolved in wash buffer.

(d) Substrate solution 60 mg. Chlorophenol red β-galactoside are dissolved in 30 ml. substrate buffer (100 mmol/liter) HEPES buffer (pH 7.1), 2 mmol/liter magnesium aspartate, 1% w/v bovine serum albumin and 0.1% w/v sodium azide).

2. Sample preparation

A blood sample is mixed with ethylenediamine-tetraacetic acid disodium salt ($EDTA-Na_2.2H_2O$). 7.5 ml. of this fresh EDTA blood are mixed with 15 ml. lysis buffer (155 mmol/liter ammonium chloride; 10 mmol/liter potassium hydrogen carbonate and 0.1 mmol/liter $EDTA-Na_2$). The mixture is left to stand for 7 to 10 minutes at ambient temperature, it thereby being carefully stirred up two or three times. Thereafter, it is centrifuged for 10 minutes at 300 g. The supernatant with the lysed erythrocytes is sucked off (Pasteur pipette, vacuum pump).

The leukocyte sediment is whirled up (Vortex mixer) and, for the lysis of residual erythrocytes, it is again resuspended in 2 ml. lysis buffer. The suspension is left to stand for 5 minutes, with occasional stirring. Thereafter, 4 ml. PBS (phosphate-buffered saline) solution (150 mmol/liter sodium chloride and 10 mmol/liter sodium phosphate buffer (pH 7.3)) is added thereto. It is again centrifuged for 10 minutes at 300 g and the supernatant is sucked off.

The cell sediment is whirled up and washed twice with, in each case, 5 ml. PBS solution. After renewed centrifuging, the supernatants are carefully sucked off. The sediment is whirled up and taken up with 2 ml. resuspension buffer (consisting of PBS solution, 0.2% w/v bovine serum albumin, 1% w/v bovine serum immunoglobin and 0.1% w/v sodium azide. This cell suspension is immediately further worked up.

3. Carrying out of the measurement

Wavelength: 578 nm
Temperature: ambient temperature (20°–25° C.)
Semimicrocuvette: 1 cm. layer thickness
Measurement volume: 1 ml; measurement against reagent blank Into centrifuge tubelets with conical bottom are pipetted:

|  | standard | | | sample |
|---|---|---|---|---|
|  | a | b | c |  |
| calibration standard suspensions a/b/c | 0.5 ml. | 0.5 ml. | 0.5 ml. | — |
| wash buffer | 2.0 ml. | 2.0 ml. | 2.0 ml. | — |

Centrifuging is carried out for 10 minutes at 300 g. The supernatants are carefully sucked off and the sediments are whirled up and then pipetted as follows:

|  | standard | | | sample |
|---|---|---|---|---|
|  | a | b | c |  |
| wash buffer | 0.2 ml. | 0.2 ml. | 0.2 ml. | — |
| cell suspension (sample from 2) | — | — | — | 0.2 ml. |
| antibody conjugate | 0.1 ml. | 0.1 ml. | 0.1 ml. | 0.1 ml. |

After thorough mixing, incubation is carried out for 45 minutes at ambient temperature (20°–25° C.) with vigorous shaking up at 15 minute intervals. Thereafter, in each case, 2 ml. wash buffer are added thereto, again mixed and centrifuged at 300 g for 10 minutes. The supernatants are carefully sucked off and the sediments whirled up. They are mixed several times with, in each case, 2 ml. wash buffer and centrifuged at 300 g for 10 minutes. The supernatants are again carefully sucked off and the sediments whirled up. Subsequently, they are resuspended with, in each case, 1 ml. substrate solution (chlorophenol red β-galactoside). They are well mixed and incubated for 30 minutes at ambient temperature (20°–25° C.), whereby, after 15 minutes and 30 minutes, in each case they are vigorously shaken and centrifuged for 5 minutes at 700 g. The extinctions of the clear supernatants are measured against the substrate solution as reagent blank.

4. Evaluation

With the help of the measured calibration standard values and the corresponding concentrations, there is produced a calibration curve. From this is directly read off the cell value for the sample corresponding to the measurement value.

EXAMPLE 2

Determination of the T-helper subpopulation

The preparation of the sample, the carrying out of the measurement and the evaluation take place in the manner described in Example 1. However, as calibration standard suspensions a, b and c, there are used suspensions which correspond to a T-helper concentration of $0.20 \times 10^6$, $0.60 \times 10^6$ and $2.08 \times 10^6$ cells/ml. Furthermore, as antibody conjugate, there is used a conjugate of a monoclonal antibody CD 4 (M-T 151, characterised in more detail in v. supra), which is specifically directed against surface antigens which are characteristic for the T-helper subpopulation, and β-galactosidase. 0.05 U Antibody are employed for each determination.

From the measured calibration standard values, there can be produced a calibration line from which can be directly read off the cell values for the sample corresponding to the measurement values.

EXAMPLE 3

Determination of the T-suppressor subpopulation

The sample preparation and the carrying out of the measurement is carried out analogously to Example 1. However, as antibody conjugate, there is used a conjugate of β-galactosidase and an antibody which is specifically directed to a surface antigen of the T-suppressor cells, CD 8 (M-T 811, characterised in more detail v. supra). For each determination, there are used 0.025 U of antibody. Furthermore, as calibration standard suspensions a, b and c, there are used three suspensions of different concentration which correspond to a T-suppressor concentration of $0.29 \times 10^6$, $0.62 \times 10^6$ and $1.17 \times 10^6$ cells/ml.

Figure 2:
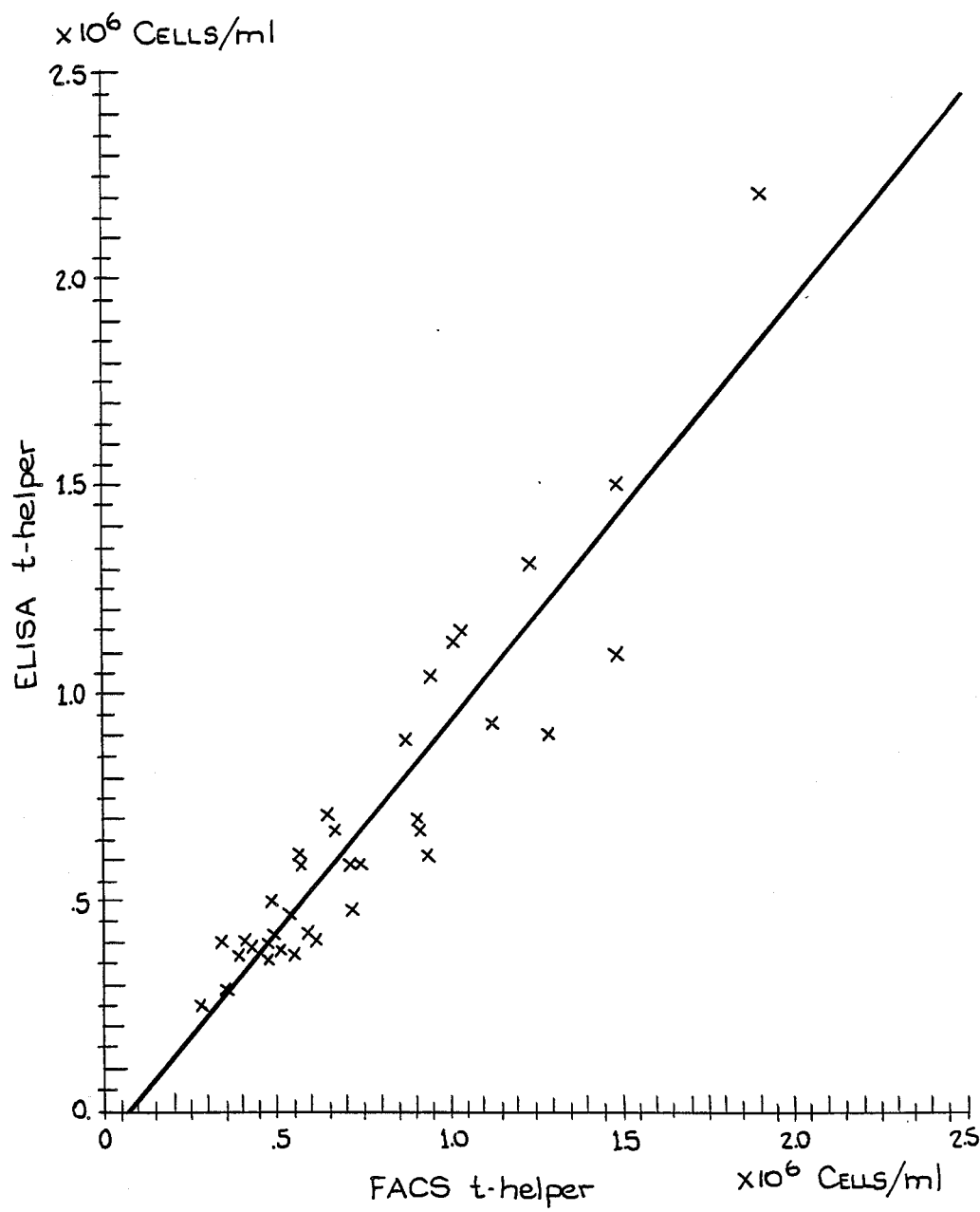
FIG. 2 shows a method comparison FACS/process according to the present invention for T-helper subpopulation (t-helper)
Figure 3:
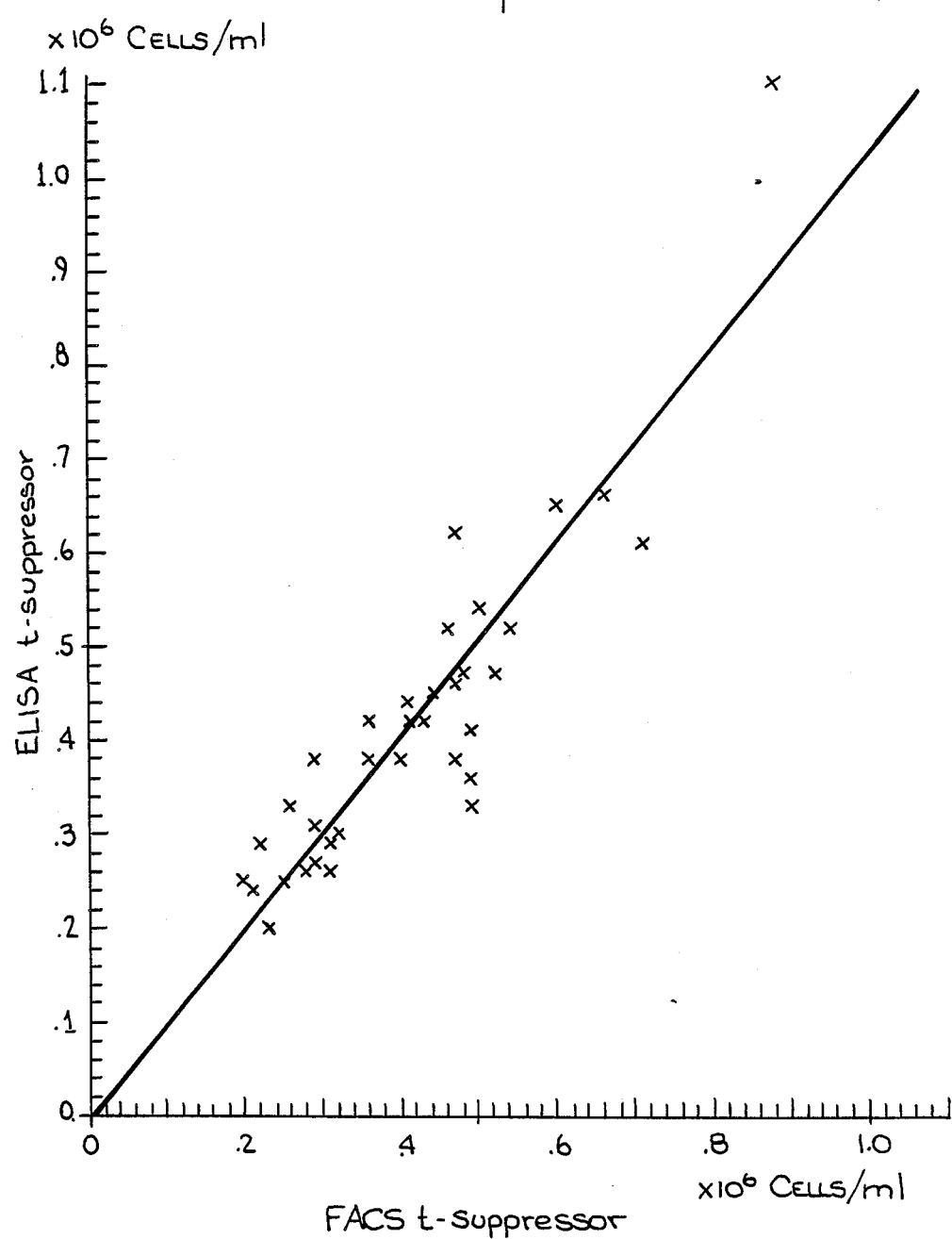
FIG. 3 shows a method comparison FACS/process according to the present invention for T-suppressor subpopulation (t-suppressor).

The results obtained with the reagent according to the present invention using the ELISA process of the present invention correlate very well with values which are obtained by the previously usual, substantially more laborious method of mechanical counting (cf. FIG. 1, FIG. 2 and FIG. 3 of the accompanying drawings.

It will be understood that the specification and examples are illustrative but not limitative of the present invention and that other embodiments within the spirit and scope of the invention will suggest themselves to those skilled in the art.

What is claimed is:

1. A process for the determination of the number of cells in a cell population or a cell subpopulation in a sample, comprising:
   (1) providing a sample of cells;
   (2) incubating said sample of cells with labelled antibodies specific to cell surface antigens of a cell population or a cell subpopulation under conditions favorable to a reaction between said cell surface antigens and said labelled antibodies, whereby the labelled antibodies complex with the cell surface antigens;

(3) providing a standard mixture of particles having a known particle concentration, said standard mixture of particles having a sedimentation behavior similar to the cells to be determined, a first portion of said mixture of particles comprising particles carrying a non-specific antibody and a second portion of said mixture of particles carrying molecules directed specifically against the labeled antibodies or a part thereof;

(4) incubating said standard mixture of particles with another portion of the labeled antibodies under conditions similar to conditions as the incubation of said sample in step (2), whereby the labeled antibodies complex with said second portions of said mixture of particles;

(5) separating the cells from the labeled antibodies that do not complex with the cell surface antigens;

(6) separating the particles from labeled antibodies that do not complex with the second portion of the mixture of particles;

(7) measuring the amount of labeling present on the separated cells and present on the separated particles; and (8) determining the number of cells by comparing a value obtained by measuring the label on said cells with value obtained by measuring label attached to said mixture of particles.

2. The process of claim 1 further comprising:

(9) providing a second standard mixture of particles having a known particle concentration and a sedimentation behavior similar to the cells to be determined, and having said first and second portions thereof mixed in a different defined proportion from that of the first standard mixture;

(10) incubating said second standard mixture of particles with another portion of labeled antibodies under conditions similar to conditions as the incubation of said sample in step (2);

(11) separating the particles from the labeled antibodies that do not complex with the second portion of the second mixture of particles;

(12) measuring the amount of labeling present on the separated particles obtained in step (11);

(13) employing the measured amount obtained in step (12) in the comparing of values in step (8).

3. The process of claim 1, wherein said labelled antibodies are labelled monoclonal antibodies.

4. The process of claim 1, wherein the label on the antibodies is a radioisotope, a dyestuff or enzyme.

5. The process of claim 4, wherein said dyestuff is a fluorescent dyestuff.

6. The process of claim 1, wherein the label on the antibodies is peroxidase, alkaline phosphatase, glucose oxidase or beta-galactosidase.

7. The process of claim 1, wherein said antibodies are antibodies against surface antigens of T-lymphocytes.

8. The process of claim 1, wherein said antibodies are antibodies against surface antigen of T-helper cell subpopulations.

9. The process of claim 1, wherein said labeled antibodies are antibodies against T-suppressor cell subpopulations.

10. A reagent kit for carrying out the process of claim 1 comprising:

a labelled antibody which is specifically directed against the cell population or subpopulation to be determined;

one or more standards comprising a mixture of particles which mixture has a sedimentation behavior similar to the population or subpopulation to be determined, a first portion of said mixture of particles carrying a non-specific antibody and a second portion of said mixture of particles carrying molecules specifically directed against said labeled antibodies or a part thereof; and a reagent for the measurement of the antibody label.

11. The reagent kit of claim 10, wherein the antibody is labelled with beta-galactosidase and the reagent is for the detection of beta-galactosidase.

* * * * *